United States Patent [19]

Brod et al.

[11] Patent Number: 4,959,213

[45] Date of Patent: Sep. 25, 1990

[54] PHARMACEUTICAL COMPOSITION FOR TREATMENT AND/OR PREVENTION OF DISEASES OF THE SKIN INVOLVING AN INFLAMMATORY PROCESS

[75] Inventors: Joel Brod; Michel Kermici, both of Paris, France

[73] Assignee: L'Oreal, Paris, France

[21] Appl. No.: 95,897

[22] Filed: Sep. 14, 1987

Related U.S. Application Data

[63] Continuation-in-part of Ser. No. 717,182, filed as PCT FR84/00253 on Nov. 7, 1984, published as WO85/0212 on May 23, 1985, abandoned.

[30] Foreign Application Priority Data

Nov. 9, 1983 [LU] Luxembourg .......................... 85081

[51] Int. Cl.$^5$ .................. A61K 37/102; A61K 35/36; C07K 15/20
[52] U.S. Cl. ..................................... 514/21; 424/543; 530/357; 530/842
[58] Field of Search .................. 530/357, 842; 424/95; 514/21

[56] References Cited

U.S. PATENT DOCUMENTS

| | | | |
|---|---|---|---|
| 3,033,755 | 5/1962 | Jacobi | 514/21 |
| 3,660,566 | 5/1972 | Vinson et al. | 424/95 |
| 4,141,888 | 2/1979 | Matsuda et al. | 530/357 |

OTHER PUBLICATIONS

Yoshino et al, Nihon Hifuka Gakkai Zasshi, 91(11), pp. 1175–1179 (1981), translation.
Yoshino, Chemical Abstracts, vol. 96: 64948e, 1982.
Baden et al, Chem. Abstracts, vol. 89: 126596e, 1978.

Primary Examiner—Jacqueline Stone
Attorney, Agent, or Firm—Cushman, Darby & Cushman

[57] ABSTRACT

A pharmaceutical composition for the treatment and prevention of erythma and acne comprises in a pharmaceutically acceptable carrier from about 1 to 10 weight percent based on the total weight of the composition of a delipidized and purified keratin polymer obtained from animal starting material containing keratin, the keratin polymer being in the free state.

6 Claims, 3 Drawing Sheets

PHARMACEUTICAL COMPOSITION FOR TREATMENT AND/OR PREVENTION OF DISEASES OF THE SKIN INVOLVING AN INFLAMMATORY PROCESS

This application is a continuation-in-part of our application, Ser. No. 717,182 filed as PCT FR/00253 on Nov. 7, 1984, published as WO85/0212 on May 23, 1985, now abandoned.

The present invention relates to a pharmaceutical composition, for treatment and prevention, in particular, by topical application, of skin diseases involving an inflammatory process, such as radiation-induced erythemas, photodermatoses, epidermolysis, acanthosis, hyperplasia, inflammations occurring in the process of carcinogenesis, inflammations of comedos in acne, seborrheic dermatoses, and the like.

Prior to the present invention various products, for application to the skin or hair, were known to contain keratin derivatives or stratum corneum cells containing keratin. Among the publications disclosing such products are:

U.S. Pat. No. 3,660,566 to Vinson et al which discloses a composition for treating the skin or hair which contains a treated stratum corneum of animal skin.

The process of producing this treated stratum corneum includes contacting the stratum corneum, in the absence of substantial amounts of the underlying epidermal tissue and other skin layers, with a solvent capable of removing barrier lipids from said stratum corneum so as to dissolve said lipids thereby leaving a suspension of tissue in the solvent. The solution is separated from the tissue and the solvent is evaporated from the solution thereby causing at least part of the lipid material to precipitate which is then recovered and employed in compositions for treating the skin.

U.S. Pat. No. 3,033,755 to Jacobi discloses a product which is employed as an ingredient in a cosmetic or pharmaceutical product to increase the moisture absorption and retaining ability of the skin. This product is prepared by removing the water soluble materials from a keratin structure. The water soluble or water and polar solvent soluble material is initially extracted from the keratin structure. The fat and wax materials are then removed from the water solution by extracton with a fat and wax solvent and the solution is neutralized to a pH in the range of 7.0 to 7.5 to precipitate the sulfur containing compounds and other skin irritating materials in the solution. The solution is concentrated and subsequently dissolved in a solvent which is compatible with a cosmetic base to be employed and the solution is then mixed with the cosmetic base.

U.S. Pat. No. 4,495,173 to Matsunga et al discloses a pre-shampoo hair treatment composition which contains a decomposition derivative of keratin material selected from the group consisting of (1) hydrolyzates of keratin material, (2) alkali salts of decomposition products obtained by oxidation of keratin material, and (3) alkali salts of derivatives at the thiol group of decomposition products obtained by reduction of keratin material. The hydrolyzates are prepared by reacting the keratin material with an acid, an alkali or an enzyme. Using an acid, the reaction is carried out at a temperature in the range of 40°–100° C. for a period of 2–24 hours. A temperature of 160° C. can be employed under pressure. The product obtained by acid hydrolysis merely undergoes hydrolysis at the polypeptide chain of keratin without involving any other changes. Using an alkali, the reaction is conducted at room temperature to 100° C. for 30 minutes to 24 hours. Using an enzyme the reaction is carried out at a temperature of 30°–45° C. for 3–24 hours. The hydrolyzates obtained from enzymes show a narrower distribution of molecular weight than hydrolyzates obtained from acid or alkalis.

As is illustrated by an abundance of literature, it has recently been discovered that the qualitative composition of the surface cutaneous lipids secreted by the skin varies between a subject having a healthy skin and a subject having a disease, or tendency to a disease, involving an inflammatory process, for example one of the diseases listed above. In particular, in the cutaneous lipid secretions present in the sebaceous glands and inside and open or closed comedo, the presence has been discovered of a sub-class of lipid products which consists of cutaneous lipids (chiefly squalene, linoleic acid and arachidonic acid) in the (per)oxidized state. These (per)-oxidized lipids and their degradation products are an irritant to the skin, and can cause serious damage by an inflamatory process if they are formed in large quantities.

Moreover, it is known that, apart from the above-mentioned cutaneous lipids which originate from the integument, there can be found, on the skin, lipids or, in general, lipid-soluble substances supplied by a treatment. A description of the "lipid-soluble substances" is provided, in particular, in European Patent Application No. 83/401,305.4 of 23 June 1983, "lipid-soluble substances" designating in general:

(a) compounds insoluble in water but soluble in polar or non-polar solvents taken alone or mixed; in this category, there are found, in particular, lipids as defined in LEHNINGER's classification (LEHNINGER—Editions Flammarion—2nd edition, chapter 11, pages 275–303);

(b) compounds soluble in one or more lipids, either alone or solubilized in one or more lipids.

In that which follows, "lipids present on the skin" will designate both the lipids which originate from the integument and the lipid-soluble substances which may have been supplied by a treatment.

The applicants have now discovered a class of compounds which, on the one hand possess very high affinity for the lipid per(oxides) present on the skin, much higher than that which they possess for the same lipids in the non-(per)oxidized state; these compounds form complex products with (per)oxidized lipids, with an interruption in the mechanism of propagation of the radicals which participate in the formation of (per)oxidized lipids; these compounds forestall, furthermore, the formation of lipid (per)oxides under the conditions of per(oxidation) by exposure to ultraviolet (A+B) radiation, and thus prevent the appearance of erythemas caused by this exposure.

This double effect of "selective pumping" of (per)oxidized lipids and protection in regard to the oxidation of the lipids in question makes this class of compounds especially useful in the treatment of inflammatory diseases of the skin ue to the lipids present on the skin in the, (per)oxidized state, since their application to the skin enables, in the first place, the lipids already (per)oxidized to be bound by forming complexes which it will be easy to remove for the purpose of detoxifying the cutaneous substrate, and, in the second place, the (per)oxidation of the lipids not yet (per)oxidized to be prevented.

Furthermore, the protective role of this class of compound in regard to the appearance of erythema under UV radiation will be stressed: it has been observed that a skin treated with a compound of this class and exposed to the sun does not show erythema; whereas an unprotected skin prone to the appearance of erythemas will be affected. Moreover, when erythema has appeared without the skin having previously been protected, the application of the abovementioned compounds performs a soothing role by trapping the per(oxidized) products formed which are in irritant to the skin. As regards the lipid-soluble substances supplied by a treatment, for example vitamin A acid, it is known that they can be the source of erythemas when the treated subject is exposed to the sun. The protective role which the abovementioned compounds can perform in these cases is clearly seen, the compounds here also forestalling and/or, as appropriate, preventing aggravation of solar erythema.

This class of compounds consist of "delipidized keratins" such as described in European Patent Application No. 83/401,305.4 of 23 June 1983.

The present invention therefore has as its subject a pharmaceutical composition for the treatment and prevention of erythema and acne comprising in a pharmaceutically acceptable carrier from about 1 to about 10 weight percent based on the total weight of said composition of a drug as defined above, i.e. a delipidized and purified keratin polymer obtained from animal starting material containing keratin, said keratin polymer being in the free state.

The pharmaceutically acceptable carrier preferably consists of water; it can, however, consist of a solvent or a fatty phase.

The pharmaceutical composition comprises delipidized and purified keratin polymer which contains from about 90 to about 95 weight percent based on the total weight of said polymer of keratin material.

The delipidized and purified keratin polymer contains at most 0.1 weight percent based on the total weight of said polymer of lipids.

The composition according to the invention can also contain an agent which promotes swelling of the keratin polymer or polymers, in the proportion of 0.3 to 2% by weight relative to the total weight of the composition. The agent which promotes the swelling of the keratin polymer or polymers is preferably urea.

The composition according to the invention can furthermore contain at least one common adjuvant taken from the group formed by penetrants, preservatives, thickeners and the like.

The composition according to the inventin can take the form of a solution, suspension, emulsion or gel.

This pharmaceutical composition contains a delipidized and purified keratin polymer which is obtained by (a) exposing the animal starting material containing keratin to ammonia vapor for 30 minutes at ambient temperature, (b) incubating the animal starting material treated in (a) at 37° C. for 1 hour in a 0.05% trypsin solution in $5 \times 10^{-2}$M tris (hydroxymethyl) aminomethane/hydrochloric acid buffer medium at pH 7.9, (c) grinding the stratum corneum obtained in (b) to a powder, solubilizing it in a "T.U.M.E." medium, dialyzing, precipitating at pH 5.5 and (d) delipidating the resulting ground animal keratin from (c) with a 2:1 v/v chloroform/methanol mixture.

The present invention also relates to process for treating or preventing skin erythema or skin acne comprising topically applying to the skin an effective amount to treat or prevent erythema or skin acne of a pharmaceutical composition comprising in a pharmaceutically acceptable carrier from about 1 to about 10 weight percent, based on the total weight of the composition, of a delipidized snd purified keratin polymer obtained from animal starting material containing keratin, said keratin polymer being in the free state.

The pharmaceutical composition according to the present invention comprises in a pharmaceutically acceptable carrier from about 1 to about 10 weight percent based on the total weight of said composition of a delipidized and purified keratin polymer obtained from animal starting material containing keratin, said keratin polymer being in the free state and being obtained by (a) subjecting said animal starting material, with stirring, for a period of time ranging from 20 minutes to 24 hours to a solvent comprising a 1–2:1 volume mixture of chloroform/methanol, respectively, or a 3:1 volume mixture of dichloromethane/methanol, (b) washing the resulting extract with a buffer, (c) dissolving the washed extract at a pH between 8.5 and 9.5 in a solubilizing medium, (d) removing the insoluble fractions and dialyzing the remaining solution, (e) precipitating keratin polymer from the dialyzate by adjusting the pH to between 5 and 5.8 and (f) recovering said keratin polymer in the free state.

According to an another embodiment of the present invention, the pharmaceutical composition for the treatment and prevention of erythema and acne comprises in a pharmaceutically acceptable carrier from about 1 to about 10 weight percent based on the total weight of said composition of delipidized and purified keratin polymer obtained from animal starting material containing keratin, said keratin polymer being in the free state and being obtained by (a) washing said animal starting material with a buffer, (b) dissolving the washed starting material at a pH between 8.5 and 9.5 in a solubilizing medium, (c) removing the insoluble fractions and dialyzing the remaining solution, (d) precipitating keratin polymer from the dialyzate by adjusting the pH to between 5 and 5.8, (e) recovering said keratin polymer in the free state, and (f) treating said keratin polymer obtained in (e) with a solvent so as to remove any remaining lipids.

The keratin polymer should preferably be completely delipidized.

The keratin polymer of the present invention has a lipid content less than 0.1 weight percent. It comprises 90 to 95 weight percent keratin material, the remainder being a non-keratin protein material.

Moreover, the starting material of animal origin used can have undergone hydrolysis and/or oxidation, either before or after delipidation.

The animal starting material, from which the keratin chains of the polymer preferably originate, is chosen from the group formed by hoof horn, especially of horses, snouts and nostrils, especially of bovines, animal hide, especially of pigs, hair and feathers, especially of chickens. The starting material can also be from human origin.

It will be stressed that the abovementioned keratin polymers are polymers in the free state, the keratin chains not being included within closed cells, as is the case, in particular, with products of keratinous origin which have undergone prior delipidation such as those defined in German Patent No. 556,488 and in U.S. Pat. Nos. 3,033,755 and 3,660,566, where the treatment of the material leaves cells in existence and the keratin polymer chains which form intracellular keratin filaments are not released. Moreover, the keratin chains forming the keratin polymer used according to the present invention are, in this polymer, at a much higher concentration than in the cell products of the abovementioned state of the art, which contain extracellular cements, intracellular non-keratinous proteins and cell membranes.

To produce the keratin polymers which can be used in the present invention, two processes in particular are available.

According to a first process, initial complete or partial delipidation is carried out by subjecting the starting material with stirring and for a time between 20 minutes and 24 hours (this time depending on the desired extent of delipidation) to the action of a solvent for the lipids present. The solvent for the delipidation is preferably a chloroform/methanol mixture in proportions between 1:1 and 2:1 by volume, or a dichloromethane methanol mixture in the proportion 3:1 by volume; advantageously it is possible to arrange that the starting material treated with the solvent is initially ground. To produce a keratin polymer from this material, a purification of known type is carried out by the following succession of stages:

(a) the extract is washed with a suitable buffer;
(b) the washed extract is solubilized at a pH between 8.5 and 9.5 in a suitable solubilizing medium;
(c) the insoluble fractions are removed and the solution is dialyzed;
(d) the keratin is precipitated by bringing the pH to between 5 and 5.8;
(e) the combination of stages (b), (c) and (d) above is optionally repeated several times;
(f) the keratin precipitated in phase (d) is recovered.

If the purification is adequate, a completely water-soluble keratin polymer is thus obtained.

Advantageously, it is possible to arrange to use for stage (a) mentioned above a buffer containing a high concentration of potassium chloride; the solubilizing medium in stage (b) is advantageously an aqueous solution ("T.U.M.E.") of tris(hydroxymethyl)aminomethane forming a buffer at pH 8.9 and containing urea (8M) and mercaptoethanol (0.2M).

According to a second process, the keratinous starting material is first, before any treatment affecting its initial loading of lipid, subjected to an extraction for producing a native keratin, in particular by the succession of stages (a) to (f) mentioned above. After this, the native keratin produced is delipidized, completely or partially, by a treatment in solvent medium similar to that used for the delipidation in the first process.

The keratin polymers used according to the present invention are completely non-toxic for the skin, by which they are very well tolerated; this is probably due to the fact that they contain keratin chains of natural origin produced from a starting material of animal origin.

It was observed that especially useful results were obtained by using, as starting materials for the keratin polymers according to the invention, keratinous materials which were very soluble in alkaline buffers containing urea, as is the case with the particular keratins listed above.

The applicants have demonstrated the greater affinity of delipidized keratins for the peroxidized form of cutaneous lipids, as well as their inhibitory effect on the peroxidation of cutaneous lipids.

(A) DEMONSTRATION OF THE EFFECT OF "SELECTIVE PUMPING" OF PEROXIDIZED LIPIDS (a) Preparation of a delipidized keratin, and loading thereof with a selected cutaneous lipid A delipidized keratin polymer is prepared according to one or other of the processes described above, and it is then reloaded with a selected cutaneous lipid.

If the first of the abovementioned processes for preparing the lipidized keratin polymer has been used, the phase of loading with lipid can be performed by bringing into contact, with stirring and for a time between 30 minutes and 12 hours according to the value desired for the degree of loading, the material to be loaded with lipid, made into particulate form, before (or after) purifying and extracting the keratin polymer, with a solution of the selected loading lipid in a solvent, and then removing the said solvent by evaporation. The excess of the loading lipid can be removed by repeated successive washings with a 0.9% strength sodium chloride solution; in the case where the loaded material has undergone a phase of purification and extraction of the keratin polymer, it is preferable to remove the excess of lipid with an aqueous "T.U.M.E." solution defined above.

If the second process defined above has been used for preparing the delipidized keratin polymer, to reload the keratin with lipid, the lipid in question is supplied in solvent medium, the reloaded keratin polymer is formed during a phase of solubilization of the keratin and this polymer is precipitated by altering the pH. The polymer is then collected by centrifugation; the excess lipid is removed with the supernatant.

The pellet can be used as it is (solid form) or resolubilized and redialyzed (solubilized form); the association of the keratinous material with the lipid is carried out in the mixture ("T.U.M.E.") defined above.

It is observed that the derivative obtained is a complex formed as a result of a destabilization of the α-helices of the keratin followed by a re-aggregation; this complex is characterized by an affinity constant similar to that defined in the mathematical model of Scatchard.

The following non-limiting examples are given to illustrate the invention.

EXAMPLE 1

First stage: Production of a keratinous starting material:

Pig hide, previously washed with water, is freed of its adipose tissue by scraping. Squares of hide 10 cm × 10 cm are placed in a chamber saturated with ammonia vapor for 30 minutes at room temperature. These squares are then incubated at 37° C. for one hour in a 0.05% strength trypsin solution in $5 \times 10^{-2}$M tris(hydroxymethyl)amino-methane/hydrochloric acid buffer medium (pH 7.9). The stratum corneum is harvested in the form of leaves, as described in the article by Fergusson, Brit. J. Dermatol. 96, 21, 1977. These leaves of stratum corneum are reduced to powder by grinding them in liquid nitrogen.

Second stage: Delipidation phase:

15 g of pig stratum corneum are solubilized in 300 ml of a T.U.M.E. mixture containing:
- urea: 6M
- mercaptoethanol: 0.2M
- tris(hydroxymethyl)aminomethane/hydrochloric acid buffer: 0.5M (pH 9).

This solubilization is performed with vigorous stirring at room temperature for 24 hours. The mixture is centrifuged to remove the undigested portion. The supernatant is dialyzed against a buffer at pH 9.

After selective-precipitation by hydrochloric acid pH 5.5, the keratin pellet is collected by centrifugation and the keratins are delipidized by means of 200 ml of chloroform/methanol 2:1 v/v. Delipidized keratins are thus obtained.

By this process, it can also be obtained a delipidized hair keratin.

Third stage: Lipid loading phase:

Keratins obtained at the end of the second stage are distributed into several 100-mg batches, and are reloaded either with degrees of loading varying from 1 to 35% of a peroxidizable, but not peroxidized, cutaneous lipid, or with degrees of loading varying from 1 to 35% of the same lipid but in its peroxidized form, which is produced by exposure under a 300 W "OSRAM ultravitalux" ® lamp with stirring in chloroform medium for 3 hours.

After evaporation of the solvents, the loaded keratins are resolubilized in T.U.M.E. medium; they are precipitated with hydrochloric acid pH 5.5 and centrifuged; the excess load is thus removed with the supernatant. Extraction of the loaded lipid substances is carried out on the pellets by means of a chloroform/methanol mixture, 2:1 v/v, with stirring for 12 hours.

(b) Determination of the maximum loading constant of a delipidized keratin with squalene and peroxidized squalene Keratins of pig stratum corneum are extracted and loaded with squalene and peroxidized squalene as described in paragraph (a) above.

Figure 1:
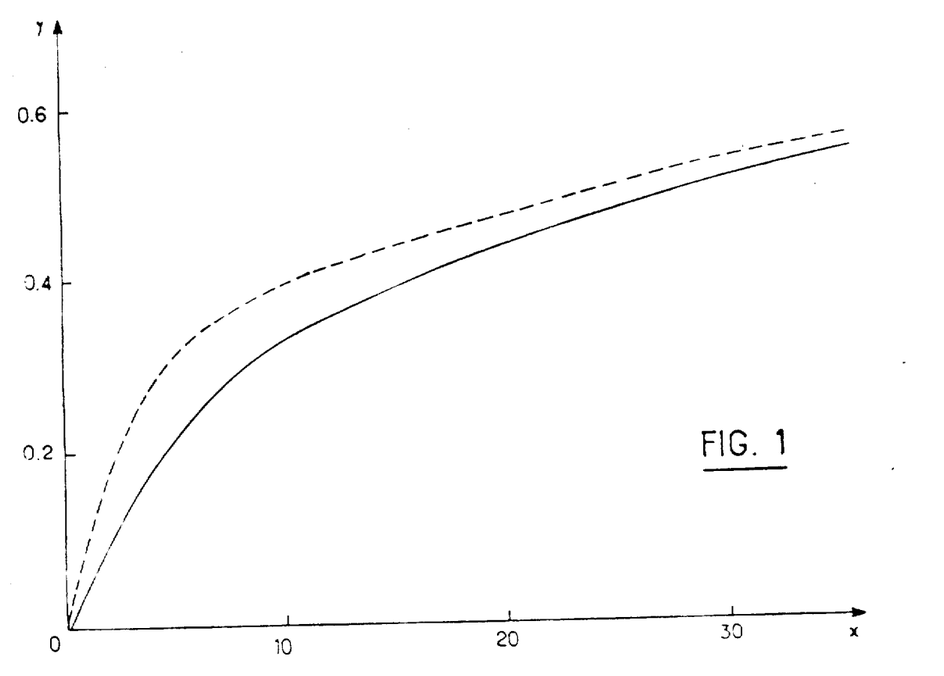

FIG. 1 of the appended drawing shows two curves, one in a continuous ine and the other in a dotted line, in which the abscissae (x) represent increasing loads of the lipid substance (respectively, non-peroxidized squalene and peroxidized squalene) expressed in mg, and the ordinates (y) represent the amount of squalene (respectively, non-peroxidized and peroxidized) expressed per unit of keratin. At small loads, a faster rate of association—indicated by the slopes at the origin—can be observed with peroxidized squalene than with non-peroxidized squalene, which allows a higher affinity of delipidized keratin to be predicted for the peroxidized form of squalene.

The practical conditions for using the delipidized keratin which form the drug according to the present invention are illustrated by the portion of the curves in FIG. 1 corresponding substantially to a value on the abscissa between 0 and 10 mg.

Figure 2:
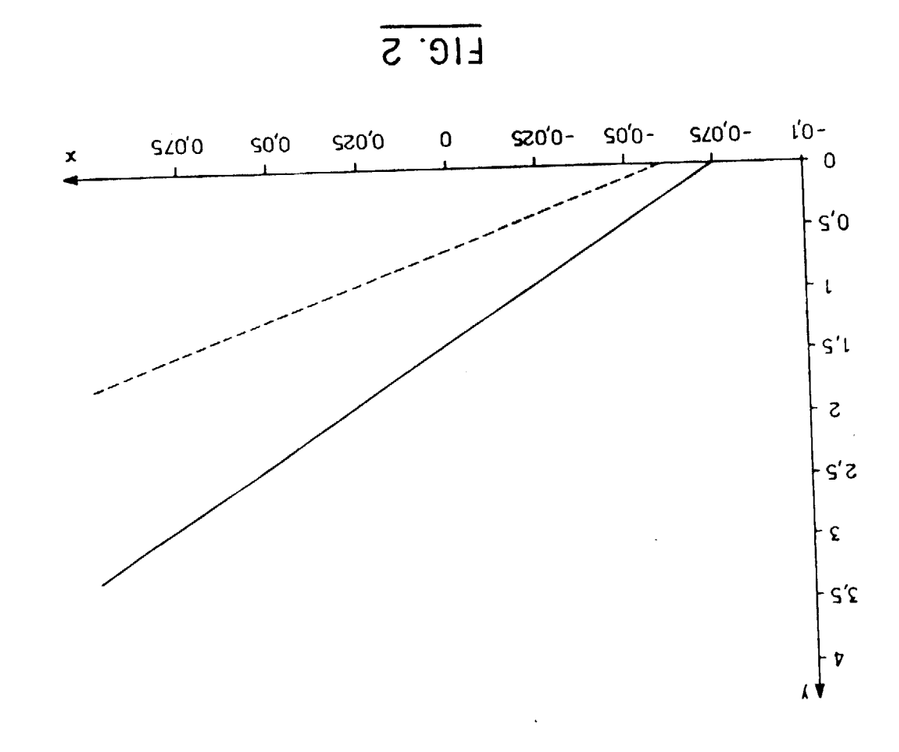

The maximal amount of load at saturation is better grasped from the inverse representation in FIG. 2, namely, the keratin/lipid (non-peroxidized and peroxidized) ratio as a function of the inverse of the amount of lipid in question (equivalent to abscissa values expressed in $mg^{-1}$ and entered in increasing order). The straight line obtained in the case of a loading with squalene (straight continuous line shown in FIG. 2) has the equation: $y = 18.7 \times + 1.4$, and that obtained in the case of a loading with peroxidized squalene (straight dotted line shown in FIG. 2) has the equation $y = 10.83 \times + 0.65$.

The point of intersection of these regression lines with the abscissa axis gives directly the inverse values of the maximum saturation constants of the keratins for, respectively, the non-peroxidized and peroxidized lipid substance, that is to say the value $1/K_s$. This value is 0.075 in the case of squalene and 0.060 in the case of peroxidized squalene. It is hence observed that the maximum loading constant is more favorable in the case of peroxidized squalene than in the case of non-peroxidized squalene.

Figure 3:
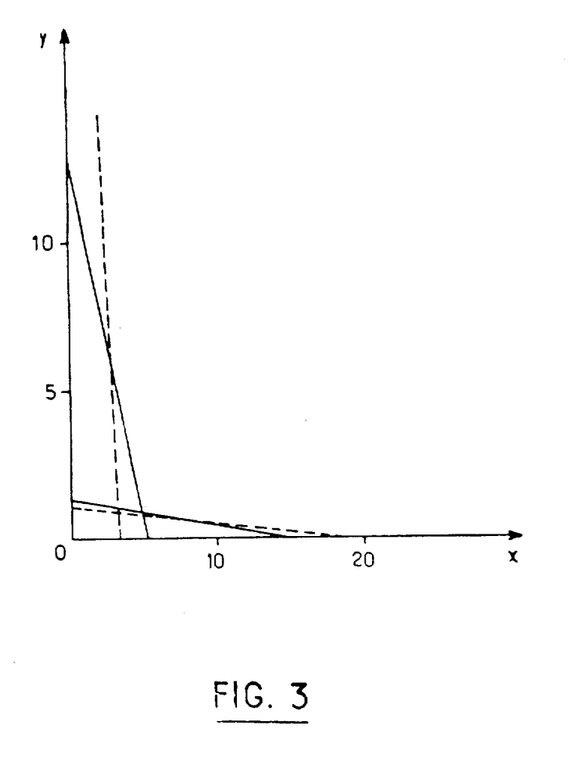

(c) Determination of the affinity constants for peroxidized and non-peroxidized squalene by representation according to the Scatchard model The abscissae (x) represent, respectively, the amount of non-peroxidized and peroxidized squalene bound, expressed in mg, and the ordinates (y) represent the ratio of bound squalene (respectively, non-peroxidized and peroxidized) to free squalene (respectively, non-peroxidized and peroxidized), which enables two asymptotic curves to be obtained in accordance with the representation of Scatchard. In FIG. 3, there are shown, with the object of simplification, in continuous lines, the tangents to the curve obtained in the case of squalene and, in dotted lines, the tangents to the curve obtained in the case of peroxidized squalene. From the slope of each of these tangents, the affinity constants are deduced, which are 2.2 in the case of squalene and 10 in the case of peroxidized squalene. It is noteworthy to observe that the affinity of keratins for peroxidized squalene is nearly five times greater than for nonperoxidized squalene. These results are in accordance with those obtained for the maximum loading constant (paragraph b).

(d) Extension to other perioxidizable lipids

The same processes forming the complex and of mathematical analysis were applied to other lipids which can also be perioxidized: linoleic acid, γ-linolenic acid and arachidonic acid. The results obtained are given in the table below.

TABLE

|  | $1/K_s$ |
| --- | --- |
| Linoleic acid | 0.025 |
| Peroxidized linoleic acid | 0.015 |
| γ-linolenic acid | 0.020 |
| Peroxidized γ-linolenic acid | 0.010 |
| Arachidonic acid | 0.060 |
| Peroxidized arachidonic acid | 0.045 |

This result shows the greatest load capacity of these lipids when they are in peroxidized form.

Moreover, a much higher affinity was also noted in the case of the peroxidized form relative to the non-peroxidized form. Thus, in the case of linoleic acid, the affinity constants, calculated as described in paragraph (c) above, are 1.3 for non-peroxidized linoleic acid and 11.9 for peroxidized linoleic acid. It follows from this that the affinity of keratins is nine times greater for the perioxidized form relative to the non-peroxidized form of linoleic acid.

From the four examples studied above, it is possible to deduce a generalized role for delipidized keratin as a trapping agent for peroxidized lipids.

(B) DEMONSTRATION OF THE PROTECTIVE EFFECT IN REGARD TO THE PEROXIDATION OF LIPIDS

(a) Demonstration in vitro

On the one hand, a batch A of a solution of 20 mg of squalene in 20 ml of a 2:1 chloroform/methanol mixture, and on the other hand a batch B of the same solution of squalene in the presence of 20 mg of delipidized keratin, are exposed for 3 hours to UV radiation at 0.353 mW/cm$^2$, each batch being stirred during the exposure.

At the end of the latter, determination of the peroxides was performed using diphenylcarbohydrazide. The determination showed that 1.4 mg of peroxidized squalene was formed in the case of batch A and 0.4 mg of peroxidized squalene in the case of batch B. In other words, 3.5 times less peroxide is formed when keratin is present in the reaction medium, which demonstrates the protective effect, by delipidized keratin, in regard to the peroxidation of squalene.

(b) Demonstration in vivo

The experiment described below is adapted from that described by W. L. Morison et al. in the article entitled "Variations in the Erythemal Response of Guinea pig Skin", in "Photo-Chemistry and Photobiology", Vol. 3, pages 283 to 285, 1981.

The delipidized keratins used are pig stratum corneum keratins at 5% concentration in a 0.3% strength urea solution in water.

Twelve albino guinea pigs receive 0.2 ml of keratin per application on a previously depilated dorsal region in an area defined by a circle 2 cm in diameter. At the same time, twelve control animals receive a placebo solution without keratin. After drying has taken place, all the animals receive either 1 or 2 minimal erythemal doses (MED) under a xenon lamp, that is to say they are exposed to the radiation produced by this lamp, respectively, for at time sufficient to cause the appearance of minimal erythema, or for twice this time.

When these erythemal doses have been applied, the intensity of the erythema is determined by the method of scoring. After mathematical treatment of the data, there are obtained the results compiled in the following table:

TABLE

|  | Mean ± standard error | Significance at 0.5%(*) |
|---|---|---|
| 1 MED | Control 2 ± 0.27 Keratin 0.75 ± 0.14 | Significant protection |
| 2 MED | Control 2.75 ± 0.28 Keratin 1.5 ± 0.22 | Significant protection |

(*)From Wilcoxon test (non-parametric data)

It has thus been demonstrated that keratins protected in vivo guinea pigs subjected to UV radiation from a xenon lamp.

The combination of the abovementioned experiments has enabled the effect of stratum corneum keratins (delipidized form) to be demonstrated in regard to (1) peroxides already formed, which are trapped by the said keratins, (2) the formation of peroxides in vitro, which formation is inhibited by the said keratins, and (3) the appearance of erythema under UV radiation, in relation to which keratins perform a protective role.

(C) DEMONSTRATION OF THE TREATING AND PREVENTIVE ACTION OF DELIPIDIZED KERATIN

The experiment described below is the rabbit ear comedogenicity test described by Kligman A. M. and Kwong T. in the article entitled "An improved rabbit ear model for assessing comedogenic substances" in "British Journal of Dermatology", vol. 100, p. 99, 1979.

The program for inducing comedos, uses male albino rabbits in which one ear is treated and the other serves as control. The ears receive one daily application for two weeks (five days out of seven—ten applications in total), to the extent of 0.1 ml of each product per ear per day. The reference comedogenic product in this case is peroxidized squalene. The delipidized keratins used are pig stratum corneum keratins at 5% concentration in a 0.3% strength urea solution in water. The peroxidized squalene and non-peroxidized squalene are applied as they are. 24 hours after the final application, the epithelium is sampled for direct observation in the stereomicroscope.

The scale and marking scheme are given in the following table:

| Non-follicular hyperkeratosis | 0 | Non-comedogenic |
|---|---|---|
| Readily visible hyperkeratosis possible presence of comedos | 1 | Slightly comedogenic |
| Readily visible comedos | 2 | Moderately comedogenic |
| Numerous large comedos | 3 | Strongly comedogenic |

The experiment comprises four groups of five animals each, treated as shown in the table below, the experiment on group I being performed with the object of verifying the absence of comedogenic activity of keratin, that on group II to demonstrate a preventive action of delipidized keratin, that on group III to demonstrate a treating action of delipidized keratin and that on group IV to verify the comedogenic activity of peroxodized squalene.

| Group | Treated ear receiving | Control ear receiving |
|---|---|---|
| I | Keratin polymer | Distilled water |
| II | Keratin polymer + peroxidized squalene (applied two hours after the keratin) | Keratin polymer + non-oxidized squalene (applied two hours after the keratin polymer) |
| III | Peroxidized squalene + keratin polymer (applied two hours after the peroxidized squalene) | Non-oxidized squalene + keratin polymer (applied two hours after the non-oxidized squalene) |
| IV | Peroxidized squalene | Non-oxidized squalene |

The results obtained are recorded in the following table:

| Groups | Products received | Grading noted 0 | 1 | 2 | 3 | Mean |
|---|---|---|---|---|---|---|
| I | Water | 5 | | | | 0 |
|  | Keratin polymer | 5 | | | | 0 |
| II | Keratin polymer + non-oxidized squalene | 3 | 2 | | | 0.4 |
|  | Keratin polymer + peroxidized squalene | | 5 | | | 1 |
| III | Non-oxidized squalene + keratin polymer | 3 | 2 | | | 0.4 |
|  | Peroxidized squalene + keratin polymer | | | 3 | 2 | 1.4 |

-continued

| Groups | Products received | Grading noted 0 | 1 | 2 | 3 | Mean |
|---|---|---|---|---|---|---|
| IV | Non-oxidized squalene | 5 | | | | 0 |
| | Peroxidized squalene | | | 4 | 1 | 2.2 |

From the above the following observations and conclusions can be made:

With regard to the Group I lots of 5 rabbits each it can be seen that all 5 rabbits in the lot treated with water and all 5 rabbits in the lot treated with keratin polymer received a grading of "0" which means that no comedogenic activity was observed.

Concerning the Group II lots of 5 rabbits each it can be seen that in the control lot, i.e., those which received the keratin polymer of the present invention 2 hours prior to the application of non-oxidized squalene, three of the 5 rabbits were graded "0" which as noted above indicates no comedogenic activity. Two of these five rabbits in the control lot were graded "1" which means only slight comedogenic activity was observed. With regard to the non-control 5 rabbit lot of Group II treated with the keratin polymer of the present invention 2 hours prior to the application of peroxidized squalene it can be seen that all 5 rabbits received a grading of "1", indicating that all five exhibited slight comedogenic activity.

With respect to the Group III lots of 5 rabbits each it can be seen that in the control lot, i.e., those which received the keratin polymer of the present invention 2 hours subsequent to the application of non-oxidized squalene, three of the 5 rabbits were graded "0" again indicating no comedogenic activity. Two of these five rabbits in the control lot were graded "1" also indicating only slight comedogenic activity. With regard to the non-control 5 rabbit lot of Group III treated with the keratin polymer of the present invention 2 hours subsequent to the application of peroxidized squalene three of the five rabbits were graded "1" indicating only slight comedogenic activity while two of the 5 rabbits were graded "2" indicating moderate comedogenic activity.

Concerning the Group IV lots of 5 rabbits each it can be seen that in the control lot, i.e., those which received nonoxidized squalene, all 5 rabbits were graded "0" indicating no comedogenic activity while 4 of the 5 non-control rabbits which received peroxidized squalene were graded "2" indicating moderate comedogenic activity and 1 non-control rabbit was graded "3" indicating strong comedogenic activity.

Thus, the values appearing in the columns under the heading "Grading noted" indicate that starting at the left hand side of these columns, i.e., starting at "0", the larger is the number of animals in each lot the less comedogenic activity is observed. Thus, as indicated above, for instance, in the Group I lot all 5 rabbits of the control lot treated with water and all 5 rabbits of the non-control lot treated with the keratin polymer of the present invention exhibited no hyperkeratosis, i.e. no comedogenic activity. On the other hand in the Group IV lots of 5 rabbits each, there is no hyperkeratosis observed for the 5 control rabbits that received non-oxidized squalene while 4 of the 5 rabbits in the non-control lot that received peroxidized squalene exhibited moderate comedogenic activity and 1 rabbit exhibiting strong comedogenic activity.

It can also be observed from the above table that when the keratin polymer of the present invention is applied two hours before the peroxidized squalene is applied the keratin polymer of the present invention is effective in substantially reducing any comedogenic activity that results. Compare the mean value of "1" for the non-control lot of 5 rabbits in Group II observed for the 2 hour pretreatment with the mean value of 2.2 for the non-control lot of 5 rabbits in Group IV.

The advantageous effects of the present invention can also be observed when the keratin polymer of the present invention is applied 2 hours after the application of peroxidized squalene. Thus, as can be seen above, a mean value of "1.4" for the non-control lot of 5 rabbits in Group III indicates a significant reduction of comedogenic activity observed compared to the mean value of 2.2 attributed to the non-control lot of 5 rabbits of Group IV.

In conclusion, the delipidized keratin polymer of the present invention lowers the comedogenic action of peroxidized squalene in both preventive treatment and treating treatment.

EXAMPLE 2

First Stage: Preparation of a sulfonic keratin derivative

Into a reactor are introduced 750 ml of pure acetic acid and 350 g of moist keratin, containing 30% of active ingredient, which has been extracted from chicken feathers with a dimethylformamide/water mixture (2.5/1 by volume) at reflux for 8 hours.

The mixture is homogenized by stirring. A mixture consisting of 375 ml of 33% by weight hydrogen peroxide and 1,125 ml of pure acetic acid is added over approximately 40 minutes, this addition being carried out with continuous cooling in an ice bath. The reaction mixture is then allowed to regain ambient temperature and stirring is continued for 15 hours. The mixture is diluted with 5 liters of water. The precipitate obtained is filtered and dried by freeze-drying. 70 g of a white powder are obtained in this way.

Second Stage: Delipidation of the keratin derivative

The delipidation of the keratin derivative obtained at the end of the first stage is carried out by means of a chloroform-methanol mixture (2/1 by volume) to complete exhaustion of the associated lipids. Completeness of the delipidation is verified by thin layer chromatography.

It was determined that the therapeutic action sought is obtained by using 0.5 to 3 mg of active principle per $cm^2$ of surface, with topical application. The period of action is variable. It can be mentioned that, when it is desired to detoxify the cutaneous substrate by removing lipid peroxides already formed, the drug can be left to act for a period of time ranging from 15 minutes to 18 hours. The skin must then be cleaned to remove the keratin/lipid peroxide complex. In the case where it is desired to treat a solar erythema, the drug composition is applied immediately, and application is repeated as many times as necessary. In the case where it is wished to prevent the appearance of an erythema, the drug composition is applied before exposure, and application is optionally repeated during and after the exposure.

EXAMPLE 3

The composition in gel form is prepared for use by topical application in the treatment of acne, this composition being formulated as follows:

| | |
|---|---|
| Delipidized keratin obtained at the end of the second stage of Example 1 described above | 5 g |
| Propylene glycol | 30 g |
| Hydroxypropylcellulose | 2 g |
| Water qs | 100 g |

When this composition was applied regularly morning and evening for 15 days to a patient whose skin had acne, a decline in the development and number of comedos was observed.

EXAMPLE 4

An oil-in-water emulsion having the following formulation is prepared:

| | |
|---|---|
| Delipidized keratin obtained at the end of the second stage of Example 1 described above | 2 g |
| Cetyl alcohol oxyethylenated with 20 moles of ethylene oxide | 0.27 g |
| Stearyl alcohol oxyethylenated with 20 moles of ethylene oxide | 0.63 g |
| Cetyl alcohol | 1.63 g |
| Stearyl alcohol | 1.47 g |
| Glycerol monostearate | 1 g |
| Liquid paraffin | 10 g |
| Water q.s. | 100 g |

This emulsion was applied to the skin of an acne subject who had undergone an acne treatment with vitamin A acid. It was observed that he was able to expose himself to the sun without skin irritation being noted.

This emulsion was, furthermore, applied to a subject suffering from solar erythema. After a few hours and two applications, it was observed that the intensity and area of the erythema had declined distinctly.

The delipidized keratin obtained at the end of the second stage of Example 2, above, can be employed in the gel of Example 3 and the emulsion of Example 4 as a replacement for the delipidized keratin obtained at the end of the second stage of Example 1.

What is claimed is:

1. A pharmaceutical composition for the treatment and prevention of erythema and acne comprising in a pharmaceutically acceptable carrier from about 1 to about 10 weight percent, based on the total weight of said composition, of a delipidized and purified keratin polymer obtained from an animal starting material comprising keratin, said keratin polymer (a) being freed from cells, (b) containing from about 90 to about 95 weight percent keratin material based on the total weight of said keratin polymer and (c) containing at most 0.1 weight percent lipid based on the total weight of said keratin polymer.

2. The pharmaceutical composition of claim 1 which also contains urea in an amount ranging from 0.3 to 2 percent by weight based on the total weight of said composition.

3. The pharmaceutical composition of claim 1 wherein said delipidized and purified polymer is obtained by (a) exposing the animal starting material to ammonia vapor for 30 minutes at ambient temperature,
   (b) incubating the animal starting material treated in (a) at 37° C. for 1 hour in a 0.05% trypsin solution in $5 \times 10^{-2}$M tris (hydroxymethyl) aminomethane/hydrochloric acid buffer medium at pH 7.9,
   (c) grinding the stratum corneum obtained in (b) to a powder, solubilizing it in a "T.U.M.E." medium, dialyzing, precipitating at pH 5.5 and
   (d) delipidating the resulting ground animal keratin from (c) with a 2:1 v/v chloroform/methanol mixture.

4. A process for treating or preventing skin erythema or skin acne comprising topically applying to the skin an effective amount to treat or prevent erythema or skin acne of a pharmaceutical composition comprising in a pharmaceutically acceptable carrier form about 1 to about 10 weight percent, based on the total weight of the composition, of a delipidized and purified keratin polymer obtained from an animal starting material containing keratin, said keratin polymer (a) being freed from cells, (b) containing from about 90 to about 95 weight percent keratin material based on the total weight of said keratin polymer and (c) containing at most 0.1 weight percent lipid based on the total weight of said keratin polymer.

5. A pharmaceutical composition for the treatment and prevention of erythema and acne comprising in a pharmaceutically acceptable carrier from about 1 to about 10 weight percent based on the total weight of said composition of a delipidized and purified keratin polymer obtained from animal starting material containing keratin, said keratin polymer being freed from cells and being obtained by (a) subjecting said animal starting material, with stirring, for a period of time ranging from 20 minutes to 24 hours to a solvent comprising a 1-2:1 volume mixture of chloroform/methanol, respectively, or a 3:1 volume mixture of dichloromethane/methanol,
   (b) washing the resulting extract with a buffer,
   (c) dissolving the washed extract at a pH between 8.5 and 9.5 in a solubilizing medium,
   (d) removing the insoluble fractions and dialyzing the remaining solution,
   (e) precipitating keratin polymer from the dialyzate by adjusting the pH to between 5 and 5.8 and
   (f) recovering said keratin polymer freed from cells.

6. A pharmaceutical composition for the treatment and prevention of erythema and acne comprising in a pharmaceutically acceptable carrier from about 1 to about 10 weight percent based on the total weight of said composition of delipidized and purified keratin polymer obtained from animal starting material containing keratin, said keratin polymer being freed from cells and being obtained by (a) washing said animal starting material with a buffer,
   (b) dissolving the washed starting material at a pH between 8.5 and 9.5 in a solubilizing medium,
   (c) removing the insoluble fractions and dialyzing the remaining solution,
   (d) precipitating keratin polymer from the dialyzate by adjusting the pH to between 5 and 5.8,
   (e) recovering said keratin polymer freed from cells, and
   (f) treating said keratin polymer obtained in (e) with a solvent so as to remove any remaining lipids.

* * * * *

UNITED STATES PATENT AND TRADEMARK OFFICE
CERTIFICATE OF CORRECTION

PATENT NO.  : 4,959,213                          Page 1 of 5

DATED       : Sept. 25, 1990

INVENTOR(S) : BROD et al

It is certified that error appears in the above-identified patent and that said Letters Patent is hereby corrected as shown below:

The 3 Drawing Sheets consisting of FIGS. 1-3 should be added as shown on the attached sheets.

The title page should be deleted to appear as per attached title page.

Signed and Sealed this

Seventh Day of May, 1991

Attest:

Attesting Officer

HARRY F. MANBECK, JR.

Commissioner of Patents and Trademarks

United States Patent [19]
Brod et al.

[11] Patent Number: 4,959,213
[45] Date of Patent: Sep. 25, 1990

[54] PHARMACEUTICAL COMPOSITION FOR TREATMENT AND/OR PREVENTION OF DISEASES OF THE SKIN INVOLVING AN INFLAMMATORY PROCESS

[75] Inventors: Joel Brod; Michel Kermici, both of Paris, France

[73] Assignee: L'Oreal, Paris, France

[21] Appl. No.: 95,897

[22] Filed: Sep. 14, 1987

Related U.S. Application Data

[63] Continuation-in-part of Ser. No. 717,182, filed as PCT FR84/00253 on Nov. 7, 1984, published as WO85/0212 on May 23, 1985, abandoned.

[30] Foreign Application Priority Data

Nov. 9, 1983 [LU] Luxembourg ............................ 85081

[51] Int. Cl.$^5$ .................. A61K 37/102; A61K 35/36; C07K 15/20
[52] U.S. Cl. ...................................... 514/21; 424/543; 530/357; 530/842
[58] Field of Search ................. 530/357, 842; 424/95; 514/21

[56] References Cited

U.S. PATENT DOCUMENTS

| | | | |
|---|---|---|---|
| 3,033,755 | 5/1962 | Jacobi | 514/21 |
| 3,660,566 | 5/1972 | Vinson et al. | 424/95 |
| 4,141,888 | 2/1979 | Matsuda et al. | 530/357 |

OTHER PUBLICATIONS

Yoshino et al, Nihon Hifuka Gakkai Zasshi, 91(11), pp. 1175–1179 (1981), translation.
Yoshino, Chemical Abstracts, vol. 96: 64948e, 1982.
Baden et al, Chem. Abstracts, vol. 89: 126596e, 1978.

*Primary Examiner*—Jacqueline Stone
*Attorney, Agent, or Firm*—Cushman, Darby & Cushman

[57] ABSTRACT

A pharmaceutical composition for the treatment and prevention of erythma and acne comprises in a pharmaceutically acceptable carrier from about 1 to 10 weight percent based on the total weight of the composition of a delipidized and purified keratin polymer obtained from animal starting material containing keratin, the keratin polymer being in the free state.

6 Claims, 3 Drawing Sheets